US007910776B2

(12) United States Patent
Straessler et al.

(10) Patent No.: US 7,910,776 B2
(45) Date of Patent: Mar. 22, 2011

(54) METHODS OF PRODUCING 1,3,5-TRIAMINO-2,4,6-TRINITROBENZENE

(75) Inventors: Nicholas A. Straessler, Plain City, UT (US); Stephen P. Velarde, Christiansburg, VA (US)

(73) Assignee: Alliant Techsystems Inc., Minneapolis, MN (US)

( * ) Notice: Subject to any disclaimer, the term of this patent is extended or adjusted under 35 U.S.C. 154(b) by 0 days.

(21) Appl. No.: 12/484,985

(22) Filed: Jun. 15, 2009

(65) Prior Publication Data

US 2010/0317894 A1 Dec. 16, 2010

(51) Int. Cl.
*C07C 213/02* (2006.01)
*C07C 205/06* (2006.01)
(52) U.S. Cl. ........................... 564/399; 568/587
(58) Field of Classification Search .................. None
See application file for complete search history.

(56) References Cited

U.S. PATENT DOCUMENTS

| | | | |
|---|---|---|---|
| 1,380,186 A | 5/1921 | Brewster | |
| 1,396,001 A | 11/1921 | MacDonald | |
| 2,246,963 A | 6/1941 | Wilkinson | |
| 3,278,604 A | 10/1966 | Hoffman et al. | |
| 3,394,183 A | 7/1968 | Dacons et al. | |
| 3,933,926 A | 1/1976 | Salter et al. | |
| 3,954,852 A | 5/1976 | Shen et al. | |
| 4,032,377 A | 6/1977 | Benziger | |
| 4,232,175 A | 11/1980 | Smith et al. | |
| 4,434,304 A | 2/1984 | DeFusco, Jr. et al. | |
| 4,745,232 A | 5/1988 | Schmitt et al. | |
| 4,952,733 A | 8/1990 | Ott et al. | |
| 4,997,987 A | 3/1991 | Ott et al. | |
| 5,371,291 A | 12/1994 | Nader | |
| 5,569,783 A | 10/1996 | Mitchell et al. | |
| 5,633,406 A | 5/1997 | Mitchell et al. | |
| 6,069,277 A | 5/2000 | Mitchell et al. | |
| 7,057,072 B2 | 6/2006 | Mitchell et al. | |
| 7,057,073 B2 | 6/2006 | Mitchell et al. | |
| 7,737,308 B1 | 6/2010 | Straessler | |
| 7,763,753 B1 | 7/2010 | Paraskos et al. | |

FOREIGN PATENT DOCUMENTS

| | | |
|---|---|---|
| GB | 2355715 A | 5/2001 |
| GB | 2355714 | 3/2004 |
| WO | 9419310 A1 | 9/1994 |

OTHER PUBLICATIONS

Agrawal, J.P., et al., Organic Chemistry of Explosives, pp. 142-143, © 2007, John Wiley & Sons Ltd., West Sussex, England.
Bellamy, A., et al., "Nitration of 1,3,5-trimethoxybenzene," J. Chem. Research (S), pp. 412-413, 2002.
Bellamy, A., et al., "Nitration of 1,3,5-trimethoxybenzene," J. Chem. Research (M), pp. 0919-0930, 2002.
Bellamy, Anthony J., et al., "A New Synthetic Route to 1,3,5-Triamino-2,4,6-Trinitrobenzene (TATB)," Propellants, Explosives, Pyrotechnics, vol. 27, pp. 49-58, 2002.

Bellamy, Anthony J., et al., "Synthesis of Ammonium Diaminopicrate (ADAP), a New Secondary Explosive," Propellants, Explosive, Pyrotechnics, vol. 27, pp. 59-61, 2002.
Bose, P.C., et al., "Occurrence of Dehydrorotenone in Derris uliginosa Benth," Indian J. Chem., vol. 14B, pp. 1012-1013, Dec. 1976.
DeFusco, A.A., et al., "An Improved Preparation of Trinitrophloroglucinol," Organic Preparations and Procedures Int., vol. 14, No. 6, pp. 393-424, 1982.
Dobratz, Brigitta M., "The Insensitive High Explosive Triaminotrinitrobenzene (TATB): Development and Characterization—1988 to 1994," Los Alamos Nat'l. Lab., LA-13014-H, History, UC-741, 151 pages, Aug. 1995.
Dove, Michael F.A., et al., "Vanadium(v) oxytrinitrate, VO(NO3)3. A powerful reagent for the nitration of aromatic compounds at room temperature under non-acidic conditions," J. Chem. Soc., Perkin Trans. 1, pp. 1589-1590, 1998.
Hoffman, D. Mark, et al., "Comparison of New and Legacy TATBs," Journal of Energetic Materials, vol. 26, pp. 139-162, 2008.
Hofmann, K.A., et al., "Verbindungen von Kobaltnitriten mit p-Toluidin, Diazoaminotoluol, Hydrazin and Nitrosohydrazin," Miteilung a. d. Chem. Laborat. D. Kgl. Akad. D. Wissenschafter zu Munchen, Eingengangen am Aug. 14, 1908, pp. 3084-3090.
Maiti, A., et al., "Solvent screening for a hard-to-dissolve molecular crystal," Physical Chemistry Chemical Physics, vol. 10, pp. 5050-5056, 2008.
Majumdar, M.P., et al., "Nitration of Organic Compounds with Urea Nitrate-Sulphuric Acid," Indian J. Chem., vol. 14B, pp. 1012-1013, Dec. 1976.
Mehilal, et al., "Studies on 2,4,6-trinitrophloroglucinol (TNPG)—A novel flash sensitizer," Indian Journal of Engineering & Materials Sciences, vol. 11, pp. 59-62, Feb. 2004.
Mellor, John M., et al., "Improved Nitrations Using Metal Nitrate—Sulfuric Acid Systems," Tetrahedron, vol. 56, pp. 8019-8024, 2000.
Mitchell, Alexander R., et al., "A New Synthesis of TATB Using Inexpensive Starting Materials and Mild Reaction Conditions," prepared for submittal to the 27th International Annual Conference of ICT, Jun. 25-28, 1996, Karlsruhe, Federal Republic of Germany, 14 pages, Apr. 1996.
Olah, George A., et al., "New Synthetic Reagents and Reactions," Aldrichimica Acta, vol. 12, No. 3, pp. 43-49, 1979.
Olah, George A., et al., Nitration Methods and Mechanisms, © 1989 VCH Publishers, Inc., New York, NY, p. 29. Ott, D.G., et al., "Preparation of 1,3,5-Triamino-2,4,6-Trinitrobenzene from 3,4-Dichloroanisole," Journal of Energetic Materials, vol. 5, pp. 343-354, 1987.
Schmidt, Robert D., et al., "New Synthesis of TATB. Process Development Studies," prepared for submittal to the JOWOG 9 (Joint Working Group 9), Aldermaston, England, Jun. 22-26, 1998, 14 pages, May 1998.
Smith, Bengt, "The Reaction between Phenols and Orthoesters. A New Synthesis of Aryl Alkyl Ethers," Acta Chem. Scand., vol. 10, No. 6, pp. 1006-1010, 1956.

(Continued)

*Primary Examiner* — Brian J Davis
(74) *Attorney, Agent, or Firm* — TraskBritt

(57) ABSTRACT

Methods of producing 1,3,5-triamino-2,4,6-trinitrobenzene (TATB), from alkoxy derivatives of phloroglucinol, such as 5-methoxyresorcinol, 3,5-dimethoxyphenol, or 1,3,5-trimethoxybenzene, are disclosed. The alkoxy derivatives may be exposed to and directly nitrated with a reaction mixture comprising a sulfuric acid solution and at least one nitrate salt. The nitrated alkoxy derivative of phloroglucinol may be alkoxylated and, thereafter, aminated to produce the TATB.

19 Claims, 1 Drawing Sheet

OTHER PUBLICATIONS

Waller, Francis J., et al., "Lanthanide(III) and Group IV metal triflate catalysed electrophilic nitration: 'nitrate capture' and the role of the metal centre," J. Chem. Soc., Perkin Trans. 1, pp. 867-871, 1999.

Zolfigol, Mohammad Ali, et al., "Nitration of Aromatic Compounds on Silica Sulfuric Acid," Bull. Korean Chem. Soc., vol. 25, No. 9, pp. 1414-1416, 2004.

Zolfigol, Mohammad Ali, et al., "Silica Sulfuric Acid/ NaNO2 as a Novel Heterogeneous System for the Nitration of Phenols under Mild Conditions," Molecules, vol. 7, pp. 734-742, 2002.

U.S. Appl. No. 11/744,986, filed May 7, 2007, entitled, "Methods of Producing 1,3,5-Triamino-2,4,6-Trinitrobenzene.".

US 7,910,776 B2

METHODS OF PRODUCING 1,3,5-TRIAMINO-2,4,6-TRINITROBENZENE

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W912HQ-07-C-0018 awarded by the Strategic Environmental Research and Development Program (SERDP).

CROSS-REFERENCE TO RELATED APPLICATIONS

This application is related to co-pending U.S. patent application Ser. No. 11/744,986 to Velarde et al., entitled "METHODS OF PRODUCING 1,3,5-TRIAMINO-2,4,6-TRINITROBENZENE," filed on May 7, 2007. This application is also related to U.S. patent application Ser. 12/484,917, now U.S. Pat. No. 7,763,753, issued Jul. 27, 2010, and U.S. patent application Ser. No. 12/484,960, now U.S. Pat. No. 7,737,308, issued Jun. 15, 2010, each of which was filed on even date herewith and assigned to the Assignee of the present application. The disclosure of each of the above-mentioned patent application and patents is incorporated by reference herein in its entirety.

TECHNICAL FIELD

The present invention, in various embodiments, relates to methods of producing 1,3,5-triamino-2,4,6-trinitrobenzene ("TATB") and, more particularly, to methods of producing TATB from alkoxy derivatives of phloroglucinol.

BACKGROUND

Nitrated TATB is an insensitive energetic material used in various military applications. TATB is used in warhead fuzes and also as the explosive component in insensitive high explosives, such as in plastic bonded explosive compositions. TATB has been produced from various starting materials, such as 1,3,5-trichlorobenzene, 3,5-dichloroanisole, trinitrobenzene, picramide, or phloroglucinol, which is also known as 1,3,5-trihydroxybenzene. While various methods of producing TATB are known, TATB is not currently available from a qualified supplier for Department of Defense applications.

TATB has been synthesized via a multistep synthesis from 1,3,5-trichlorobenzene ("TCB") using a process that generates environmentally problematic organic and salt waste streams.

Another method of synthesizing TATB from phloroglucinol is described in GB 2355715. The phloroglucinol is nitrated using sodium nitrite and nitric acid, forming trinitrophloroglucinol ("TNPG"), which is also known as 1,3,5-trihydroxy-2,4,6-trinitrobenzene. The nitric acid is added sequentially or in multiple additions. When cooled, a solid is produced, which is filtered, washed with 3M hydrochloric acid ("HCl"), and dried, yielding a solid product that is a monohydrate of TNPG. The monohydrate of TNPG is a free-flowing solid. The TNPG is alkoxylated using a trialkyl orthoformate, such as triethyl orthoformate ("TEOF"), forming 1,3,5-triethoxy-2,4,6-trinitrobenzene ("TETNB"). The alkoxylation of TNPG requires a ninefold molar excess of triethyl orthoformate, producing a waste stream of ethyl formate, ethanol, and diethyl ether. The ethanol and ethyl formate are removed by distillation. The solution of TETNB is concentrated, yielding TETNB as a solid, which is recrystallized from ethanol. The purified TETNB is aminated using liquid ammonia, filtered, washed with N-methylpyrrolidinone and methanol, and dried, yielding crystals of the TATB. The TATB synthesis utilizes multiple drying and isolation acts to produce solid products of TNPG, TETNB, and TATB.

Since intermediates formed during the TATB synthesis are sensitive to impact, friction, or electrostatic discharge ("ESD"), or are otherwise dangerous to handle, it would be desirable to minimize exposure of personnel and equipment to the intermediates. In addition, it would be desirable to reduce the amount of labor and time needed to produce the TATB and to improve the purity of the TATB and TETNB.

BRIEF SUMMARY OF THE INVENTION

In some embodiments, the present invention includes a method of producing 1,3,5-triamino-2,4,6-trinitrobenzene that includes exposing at least one alkoxy derivative of phloroglucinol to a reaction mixture including at least one nitrate salt and a sulfuric acid solution to form a nitrated product, reacting the nitrated product with an alkoxylating agent to form 1,3,5-trialkoxy-2,4,6-trinitrobenzene and reacting the 1,3,5-trialkoxy-2,4,6-trinitrobenzene with an aminating agent to form 1,3,5-triamino-2,4,6-trinitrobenzene.

In additional embodiments, the present invention includes a method of producing 1,3,5-triamino-2,4,6-trinitrobenzene, which includes exposing 1,3,5-trimethoxybenzene to a reaction mixture comprising at least one nitrate salt and a sulfuric acid solution to form 1,3,5-trimethoxy-2,4,6-trinitrobenzene and reacting the 1,3,5-trialkoxy-2,4,6-trinitrobenzene with an aminating agent.

In yet another embodiment, the present invention includes a method of producing 1,3,5-trimethoxy-2,4,6-trinitrobenzene. The method may include exposing at least one alkoxy derivative of phloroglucinol to a reaction mixture comprising at least one nitrate salt and a sulfuric acid solution to form a nitrated product and reacting the nitrated product with an alkoxylating agent in an organic solvent to form 1,3,5-trimethoxy-2,4,6-trinitrobenzene.

BRIEF DESCRIPTION OF THE DRAWINGS

While the specification concludes with claims particularly pointing out and distinctly claiming that which is regarded as the present invention, advantages of this invention may be more readily ascertained from the following description of the invention when read in conjunction with the accompanying drawings in which:

DETAILED DESCRIPTION OF THE INVENTION

Figure 1:
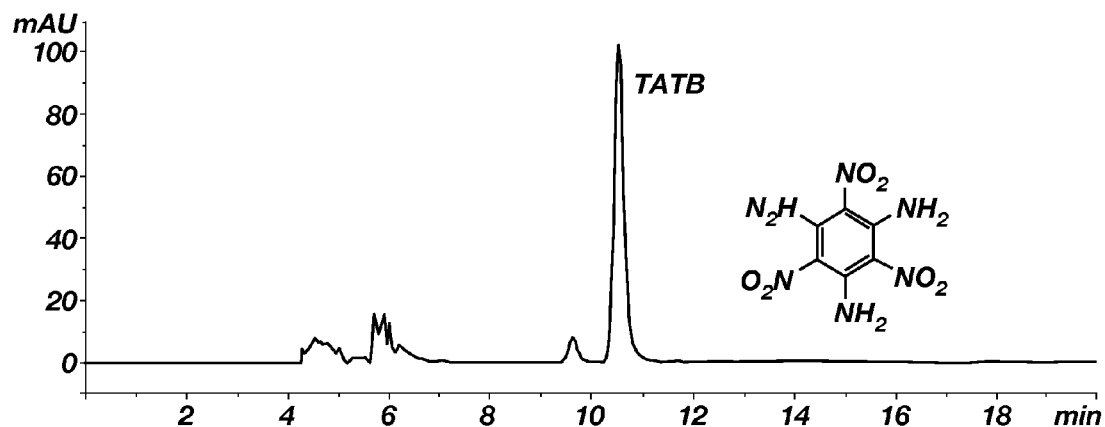
FIG. 1 is a chromatogram of TATB formed by the process described in Example 1 and obtained using high-performance liquid chromatography (HPLC)

As used herein, the terms "comprising," "including," "containing," "characterized by," and grammatical equivalents thereof are inclusive or open-ended terms that do not exclude additional, unrecited elements or method steps, but also include the more restrictive terms "consisting" of and "consisting essentially of" and grammatical equivalents thereof. As used herein, the term "may" with respect to a material, structure, feature, or method act indicates that such is contemplated for use in implementation of an embodiment of the invention and such term is used in preference to the more restrictive term "is" so as to avoid any implication that other compatible materials, structures, features, and methods usable in combination therewith should, or must be, excluded.

A method of producing TATB from an alkoxy derivative of phloroglucinol is disclosed. As used herein, the terms "alkoxy derivative of phloroglucinol" and "alkoxy derivative" mean and include a mono-, di-, or tri-alkoxylated derivative of phloroglucinol, such as 5-methoxyresorcinol, 3,5-dimethoxyphenol, or 1,3,5-trimethoxybenzene. Alkoxy derivatives of phloroglucinol (5-methoxyresorcinol, 3,5-dimethoxyphenol, or 1,3,5-trimethoxybenzene) are commercially available, such as from Sigma-Aldrich Co. (St. Louis, Mo.). Alternatively, the alkoxy derivatives may be synthesized from glucose, a renewable feedstock, serving to even further reduce the environmental impact of TATB synthesis.

In one embodiment, an alkoxy derivative of phloroglucinol is nitrated to form a mono-, di-, or tri-nitrated intermediate. The mono- or di-nitrated intermediates are alkoxylated, forming a 1,3,5-trialkoxy-2,4,6-trinitrobenzene, which is aminated to produce the TATB. An exemplary reaction scheme for producing TATB from the alkoxy derivatives (methoxy derivatives) is shown below:

nitrate salts and the sulfuric acid are commercially available from various sources, such as from Sigma-Aldrich Co. (St. Louis, Mo.). An exemplary reaction scheme for producing the tri-nitrated intermediate from the alkoxy derivative of phloroglucinol is shown below:

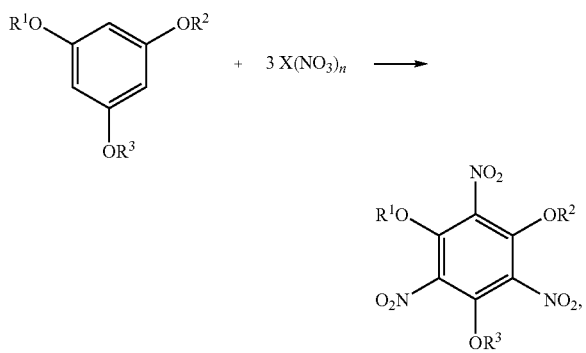

where each of $R^1$, $R^2$, and $R^3$ are independently H or an alkyl, but $R^1$, $R^2$, and $R^3$ are not all H, and X is $Na^+$, $K^+$, $NH_4^+$, $Ca^{2+}$, or $Mg^{2+}$. While specific examples describe using methoxy derivatives of phloroglucinol, the alkyl may be methyl, ethyl, or propyl. While specific examples below describe using

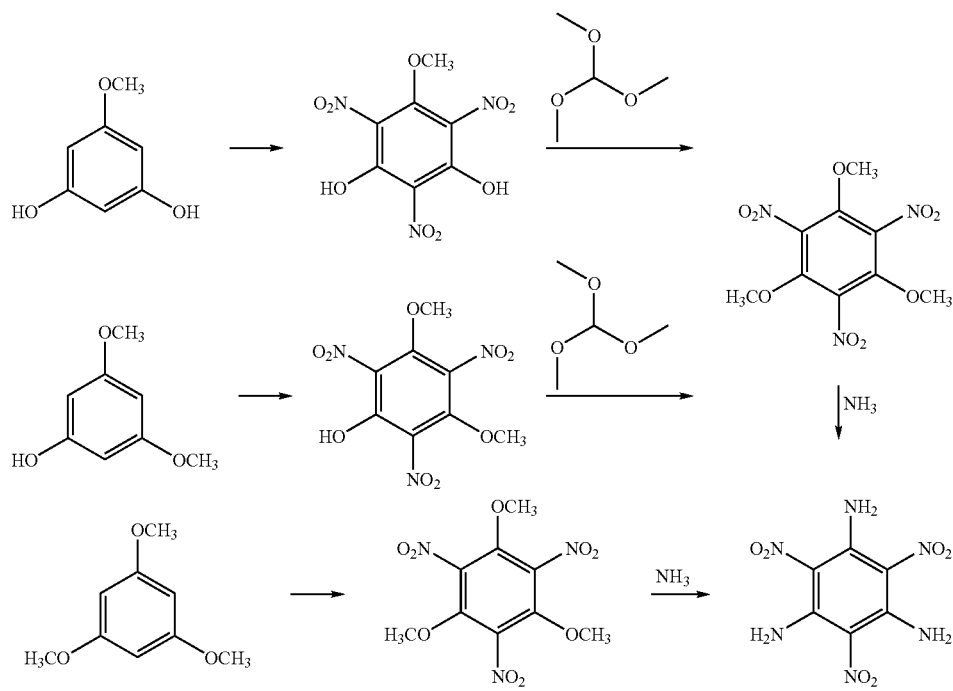

The alkoxy derivative may be directly nitrated using a mixture of a nitrate salt and sulfuric acid ($H_2SO_4$). The term "directly nitrated" means and includes nitrating the alkoxy derivative of phloroglucinol, which is a nitratable aromatic compound, in a single reaction act, without forming an intermediate compound, which is then subsequently nitrated. The nitration reaction produces a nitrated alkoxy derivative, such as the mono-, di-, or tri-nitrated intermediates. The nitrate salt may be sodium nitrate ($NaNO_3$), potassium nitrate ($KNO_3$), ammonium nitrate ($NH_4NO_3$), calcium nitrate ($Ca(NO_3)_2$), magnesium nitrate ($Mg(NO_3)_2$) or combinations thereof. The ammonium nitrate as the nitrate salt, other nitrate salts may be used. In addition, mixtures of nitrate salts may be used. While the reaction scheme above illustrates that three molar equivalents of the nitrate salt may be used relative to the nitratable aromatic compound, one or two molar equivalents of the nitrate salt may be used to produce a mono- or di-nitrated alkoxy derivative.

By way of non-limiting example, the alkoxy derivative may be nitrated to form a mono-, di- or tri-nitrated compound. Nitration of the alkoxy derivatives described herein may be performed as described in co-pending U.S. Pat. No. 7,737, 308. Reaction schemes for producing 5-methoxystyphnic acid (5-methoxy-2,4,6-trinitroresorcinol) from 5-methoxyresorcinol, 3,5-dimethoxypicric acid (3,5-dimethoxy-2,4,6-trinitrophenol) from 3,5-dimethoxyphenol, and 1,3,5-trimethoxy-2,4,6-trinitrobenzene from 1,3,5-trimethoxybenzene are shown below:

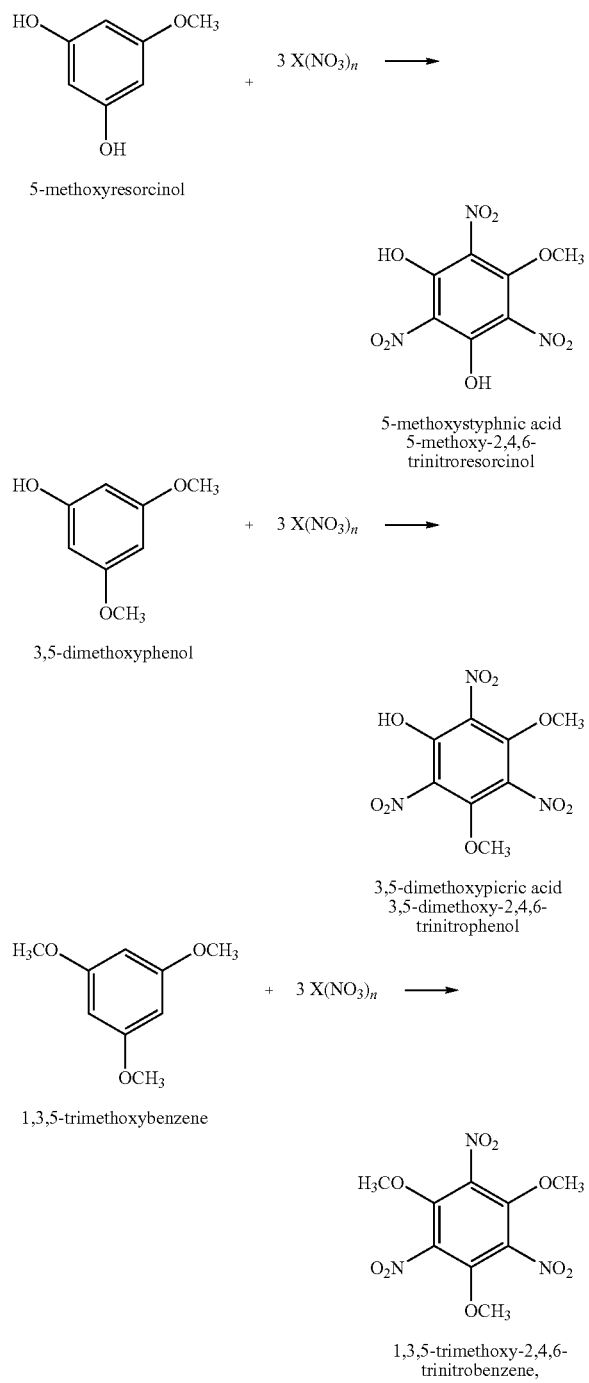

where X is $Na^+$, $K^+$, $NH_4^+$, $Ca^{2+}$, or $Mg^{2+}$. In addition, mixtures of nitrate salts may be used. While the reaction scheme above illustrates that three molar equivalents of the nitrate salt may be used relative to the alkoxy derivative, one or two molar equivalents of the nitrate salt may be used to produce a mono- or di-nitrated alkoxy derivative.

The alkoxy derivative may be nitrated using a mixture of the at least one nitrate salt and sulfuric acid. Water may, optionally, be present in the nitrate salt/sulfuric acid mixture. To nitrate the alkoxy derivative, a sulfuric acid solution may be added to a reaction vessel and may be cooled to a temperature within a range of from about 0° C. to about 10° C. The reaction vessel is compatible with the conditions of the nitration reaction, and may be a round-bottom flask or a reactor. For the sake of example only, when commercial quantities of the alkoxy derivative are to be produced, the reaction vessel may be a 5-, 50-, or 500-gallon Pfaudler type glass-lined reactor. In one embodiment, the sulfuric acid solution is cooled to a temperature of about 5° C. before adding the nitrate salt. The temperature of the sulfuric acid solution may be reduced using a cooling source, such as an ice water bath, to cool the reaction vessel. The sulfuric acid solution may include between about 80% by weight (wt %) and about 100 wt % sulfuric acid and between about 0 wt % and about 20 wt % water. Particularly, the sulfuric acid solution may include between about 90 wt % and about 100 wt % sulfuric acid and between about 0 wt % and about 10 wt % water. In one embodiment, the sulfuric acid solution includes about 96 wt % sulfuric acid and about 4 wt % water, which is known in the art as "concentrated sulfuric acid." The concentrated sulfuric acid may react violently with water if mixed quickly and, thus, may be handled in a fume hood.

After cooling, the nitrate salt may be slowly added to, and combined with, the sulfuric acid solution in the reaction vessel to form the nitrate salt/sulfuric acid mixture. A stoichiometric equivalent of the nitrate salt may be dissolved in the sulfuric acid solution. Depending on the desired degree of nitration of the alkoxy derivative, the amount of nitrate salt added to the reaction vessel may be a molar equivalent or greater, relative to the alkoxy derivative. If an alkoxy derivative having one nitro group is to be produced, one mole of the nitrate salt may be added to the reaction vessel per mole of the alkoxy derivative. If two or three nitro groups are to be present on the alkoxy derivative, two moles or three moles, respectively, of the nitrate salt may be added to the reaction vessel per mole of the alkoxy derivative. The nitrate salt/sulfuric acid mixture may be a solution or a suspension. The nitrate salt may be added to the sulfuric acid solution while stirring at a rate such that the temperature of the sulfuric acid solution does not exceed about 30° C., and more particularly about 10° C. To maintain the sulfuric acid solution at this temperature, the reaction vessel may be continuously cooled during addition of the nitrate salt while stirring. Combining the nitrate salt with the sulfuric acid solution produces a lower exotherm compared to the exotherm produced during conventional techniques of nitrating phloroglucinol, such as when nitric acid and sulfuric acid are combined. The alkoxy derivative may be added to the nitrate salt/sulfuric acid mixture to form a reaction mixture. The alkoxy derivative may be added to the reaction mixture, for example, stepwise, continuously or in a single portion. The temperature of the nitrate salt/sulfuric acid mixture may, optionally, be reduced to less than or equal to about 5° C. before adding the alkoxy derivative. Substantially all of the sulfuric acid and nitrate salt may be present in the reaction vessel before adding the alkoxy derivative.

After adding the alkoxy derivative, the cooling source may be removed and the temperature of the reaction mixture may increase. Once the cooling source is removed, the temperature of the reaction mixture may increase due to the exothermic nature of the nitration reaction. Optionally, the reaction mixture may be heated to a temperature in a range of from about 0° C. to about 27° C. and, more particularly, about 25° C. In some embodiments, after the reaction mixture has increased to ambient temperature (i.e., between about 23° C. and about 27° C.), the temperature of the reaction mixture may be increased to between about 30° C. and about 70° C. and, more particularly, about 55° C. Upon addition of the alkoxy derivative to the nitrate salt/sulfuric acid mixture, the alkoxy derivative may become directly nitrated, producing the mono-, di- or tri-nitrated alkoxy derivative.

The reaction mixture may, optionally, be stirred for from about 1 minute to about 30 minutes to produce a mixture of the nitrated alkoxy derivatives and byproducts or contaminants. Continuous stirring may facilitate the nitration reaction by providing adequate mixing of the reactants. In one embodiment, the reaction mixture is stirred for about 10 minutes. The nitrated alkoxy derivative may then be precipitated by cooling the reaction mixture to a temperature of from about 0° C. to about 25° C. The slurry or solution may be cooled, for example, by adding it to crushed ice, or ice water, or a mixture thereof and stirring for about 10 minutes to about 60 minutes or until substantially all of the ice has melted.

The nitrated alkoxy derivative has a low solubility in the aqueous, acidic solution, enabling the nitrated alkoxy derivative to precipitate from the reaction mixture. The resulting acid-wet nitrated alkoxy derivative may be substantially free of the byproducts or contaminants. The yield of the nitrated alkoxy derivative may be from about 50% to about 95%, and the purity of the nitrated alkoxy derivative may be from about 95% to about 99%. The nitrated alkoxy derivative may be a mono-, di-, or tri-nitrated compound depending on the amount of nitrate salt used in the nitration reaction. The nitrated alkoxy derivative may include, but is not limited to, 5-methoxystyphnic acid, 3,5-dimethoxypicric acid, or 1,3,5-trimethoxy-2,4,6-trinitrobenzene.

Once cooled, an extraction process may be performed to remove the nitrated alkoxy derivative from the aqueous, acidic solution. The nitrated alkoxy derivative may be extracted from the nitration mixture with an organic solvent. By way of non-limiting example, the organic solvent may include an acetic ester, such as, ethyl acetate or butyl acetate ($C_6H_{12}O_2$). The nitrated alkoxy derivative may be transferred to a separatory funnel and from about 150 mL to about 250 mL of ethyl acetate per gram of alkoxy derivative may be introduced to the aqueous, acidic solution containing the nitrated alkoxy derivative to form a nitrated product/organic solvent solution. By employing an organic solvent, such as ethyl acetate, in the extraction process, the use of additional solvents, such as toluene and methanol, in the ensuing alkylation and amination reactions is eliminated.

The nitrated alkoxy derivative may then be purified using a conventional technique such as, for example, chromatography or filtration. By way of non-limiting example, the nitrated alkoxy derivative/organic solvent solution may be chromatographed on a column including silica gel, while eluting with additional organic solvent, e.g., ethyl acetate, to remove the nitrated alkoxy derivative from the silica gel. In some embodiments, the nitrated alkoxy derivative may include at least one of 5-methoxystyphnic acid, 3,5-dimethoxypicric acid, and 1,3,5-trimethoxy-2,4,6-trinitrobenzene, which may be separated from one another using conventional techniques. Alternatively, the nitrated alkoxy derivative may be purified by drying the nitrated product/organic solvent solution over magnesium sulfate ($MgSO_4$). The magnesium sulfate may then be removed using a conventional filtration process and may be rinsed with additional organic solvent, such as ethyl acetate. The ethyl acetate used to rinse the magnesium sulfate may be collected with the nitrated alkoxy derivative.

After producing and, optionally, purifying the nitrated alkoxy derivative, an alkoxylation reaction followed by an amination reaction may be performed to produce TATB. The alkoxylation reaction may be performed to alkoxylate the nitrated mono- and di-alkoxy derivatives, such as 5-methoxystyphnic acid and 3,5-dimethoxypicric acid, by adding an alkoxylating agent. The nitrated alkoxy derivative in the organic solvent may be introduced to a reaction vessel. In some embodiments, the alkoxylation reaction may be performed in the same reaction vessel in which the nitration reaction was performed. In the reaction vessel, the nitrated product/organic solvent solution may be concentrated to promote the alkoxylation reaction. A conventional rotary evaporator may be used to concentrate the nitrated product/organic solvent solution at a pressure of about 1 inHg to about 30 inHg and a temperature of from about 30° C. to about 77° C. The higher the vacuum (less pressure), the lower the temperature of the heating bath needs to be to remove the solvent. The solvent removed by this method is very pure when collected and can be reused in subsequent extractions and rinses.

In some embodiments, the alkoxylating agent is a trialkyl orthoformate, such as trimethyl orthoformate (TMOF), TEOF, tripropyl orthoformate or mixtures thereof. Each of these alkoxylating agents is commercially available from various sources, such as from Sigma-Aldrich Co. A sufficient amount of the alkoxylating agent may be added to the nitrated product/organic solvent solution such that the alkoxylation reaction proceeds substantially to completion. By way of non-limiting example, about four molar equivalents of the alkoxylating agent may be used relative to a nitrated mono-alkoxy derivative (i.e., 5-methoxystyphnic acid), or about two molar equivalents of the alkoxylating agent may be used relative to a nitrated di-alkoxy derivative (i.e., 3,5-dimethoxypicric acid), to produce a nitrated tri-alkoxy derivative (i.e., 1,3,5-trialkoxy-2,4,6-trinitrobenzene).

Alkoxylating the nitrated alkoxy derivatives forms 1,3,5-trialkoxy-2,4,6-trinitrobenzene, which remains dissolved in the organic solvent to form a 1,3,5-trialkoxy-2,4,6-trinitrobenzene/organic solvent solution. Additional organic solvent may, optionally, be added to maintain an initial volume of the organic solvent in the reaction vessel such that the 1,3,5-trialkoxy-2,4,6-trinitrobenzene remains in solution. For example, the additional organic solvent may be added to the reaction vessel to maintain a volume of from about 10 mL to about 50 mL. In one embodiment, TMOF is used as the alkoxylating agent and is reacted with the 5-methoxystyphnic acid or 3,5-dimethoxypicric acid, producing 1,3,5-trimethoxy-2,4,6-trinitrobenzene. While the example described herein utilizes TMOF as the alkoxylating agent, triethyl orthoformate or tripropyl orthoformate may be used to form 1,3,5-triethoxy-2,4,6-trinitrobenzene or 1,3,5-tripropoxy-2,4,6-trinitrobenzene, respectively.

The nitrated alkoxy derivative and the alkoxylating agent may be stirred to form a solution. The alkoxylation reaction may be conducted at a temperature within a range of from about 75° C. to about 120° C., dependent on the boiling point of the solvent. If the temperature is significantly higher than the boiling point of the solvent, the alkoxylating agent may be volatilized before reacting with the nitrated alkoxy derivative. If the temperature is significantly lower than the boiling point of the solvent, such as less than about 70° C., the alkoxylation reaction may proceed too slowly to be economical. A low temperature may also cause insufficient amounts of volatile byproducts to be removed during the reaction. As a non-limiting example, the reaction mixture may be heated to a temperature of about the boiling point of the organic solvent, i.e., about 77° C. for ethyl acetate, to induce a reflux phenomenon. Substances in the reaction mixture having a boiling point lower than the reflux temperature may be released as a vapor and removed by conventional fractional distillation.

The alkoxylation reaction may be conducted at atmospheric pressure for a sufficient amount of time to achieve mono- or di-alkoxylation of the nitrated alkoxy derivative. The alkoxylation reaction may also be conducted at reduced pressure if a lower reaction temperature is desired. The reaction time may vary depending on the reaction size. The reflux may be performed until substantially all of the nitrated alkoxy derivative has been alkoxylated. As a non-limiting example, the reaction may be refluxed for between about 24 hours and about 72 hours. Progress of the alkoxylation reaction may be monitored by conventional techniques, such as by high performance liquid chromatography ("HPLC"), by proton nuclear magnetic resonance ("proton NMR") spectroscopy or by thin layer chromatography ("TLC"). However, even if the nitrated alkoxy derivatives are under-reacted, the alkoxylation reaction may achieve desirable yields.

After the nitrated alkoxy derivative has been alkoxylated, an extraction process may be conducted to remove the non-volatile impurities and excess (unreacted) alkoxylating agent. For example, the nitrated alkoxy derivative may be transferred to a separatory funnel and washed with an aqueous sodium bicarbonate solution ($NaCO_3$), i.e., 10% sodium bicarbonate, to form an aqueous layer and an organic layer. The aqueous layer may then be removed and discarded and the organic layer may be dried. As a non-limiting example, the organic layer may be dried over magnesium sulfate and the magnesium sulfate may be removed by conventional filtration techniques and rinsed with a minimal amount of the organic solvent, such as ethyl acetate.

The 1,3,5-trialkoxy-2,4,6-trinitrobenzene may be reacted with an aminating agent to form a reaction mixture including TATB. The filtrate including the 1,3,5-trialkoxy-2,4,6-trinitrobenzene may be diluted in the reaction vessel with the organic solvent (e.g., ethyl acetate). The aminating agent may be introduced to the reaction vessel while stirring. The aminating agent may be ammonia (liquid or gaseous) or ammonium hydroxide (aqueous ammonia). The flow rate of the aminating agent may be less than about 1 standard cubic feet/min (SCFM). The aminating agent may be flowed through the diluted 1,3,5-trialkoxy-2,4,6-trinitrobenzene/organic solvent solution for a sufficient amount of time that a solid is produced. Upon adding the aminating agent, the 1,3,5-trialkoxy-2,4,6-trinitrobenzene is aminated to TATB. To provide a substantially complete reaction, the TATB reaction mixture may be stirred, for example, for about 1 hour to about 10 hours and, more particularly, about 6 hours. The pressure may range from approximately 1 pound per square inch ("psi") to approximately 200 psi. In one embodiment, the pressure ranges from approximately 40 psi to approximately 50 psi. The solids may be collected by filtration and washed with additional reaction solvent and then with distilled water. A third wash may be performed with ethyl acetate, methanol, isopropanol, other alcohol, or other organic solvent. The TATB may then be dried (water removed), such as by a conventional vacuum filtration process, producing substantially anhydrous crystals of the TATB.

By using a combination of a nitrate salt and sulfuric acid for the nitration reaction, the reaction times, reaction temperatures and the amount of starting materials for the nitration reaction are reduced compared to conventional techniques. Nitrating alkoxy derivatives of phloroglucinol using the nitrate salt and sulfuric acid provide complete nitration in about 1 hour at a temperature of about 25° C. In addition, the nitration reaction produces fewer undesirable byproducts and uses starting materials having increased stability, reduced toxicity and reduced cost. Specifically, the nitrate salts have a substantially increased stability in comparison to reagents, such as nitric acid, which are used in conventional nitration processes. The nitrate salts are also more economical, have a longer shelf life, and are less hazardous than the mixture of acids (nitric acid and sulfuric acid) currently used to nitrate phloroglucinol when manufacturing TATB. Furthermore, the nitrate salts are much easier to handle and enable the reaction to take place in substantially increased anhydrous conditions, if desirable. The present method of nitrating the alkoxy derivatives also reduces or eliminates the production of nitrogen oxides ($NO_x$) that are formed using conventional nitration processes. In addition, the sulfuric acid is partially neutralized by the nitrate salt during the nitration reaction, reducing the amount of spent sulfuric acid to be disposed of.

In comparison to conventional TATB synthesis techniques, using alkoxy derivatives of phloroglucinol as starting materials results in substantially reduced amounts of the alkoxylating agent, such as trimethylorthoformate, being used in the alkoxylation reaction. Synthesis of TATB from alkoxy derivatives of phloroglucinol may also reduce or eliminate waste streams associated with orthoformates used during conventional TATB synthesis techniques. Since trialkyl orthoformates constitute a substantial portion of the cost of synthesizing TATB by conventional techniques, synthesizing TATB from the methoxylated derivatives of phloroglucinol substantially reduces the cost associated with synthesizing TATB. By enabling TATB formation in a single solvent, the present method of forming TATB provides improved safety by reducing handling of hazardous or sensitive intermediates.

The following examples serve to explain embodiments of the present invention in more detail. These examples are not to be construed as being exhaustive or exclusive as to the scope of this invention.

EXAMPLES

Example 1

Synthesis of TATB from 3,5-Dimethoxyphenol (3,5-DMP)

Sulfuric acid (30 mL (96%)) was placed in a 250-ml round-bottom flask equipped with a cooling bath and a magnetic stirrer and the round-bottom flask was cooled to about 5° C. Sodium nitrate (1.64 g (19.3 mmol)) was added to the round-bottom flask at a rate such that the temperature did not exceed about 10° C. The temperature of the round-bottom flask was reduced to about 5° C. and 3,5-DMP (1 g (6.49 mmol)) was added thereto. The 3,5-DMP was added to the round-bottom flask at a rate such that the temperature did not exceed about 15° C. After addition of the 3,5-DMP, the cooling bath was removed, and the mixture was stirred for about 20 minutes. The reaction mixture was added in a single portion to crushed ice (about 200 g) to form an aqueous suspension and was gently stirred until the ice had substantially melted. The aqueous solution was added to a separatory funnel and the product, 3,5-dimethoxypicric acid (DMPA), was extracted with ethyl acetate (1×100 mL, 2×50 mL). The DMPA/ethyl acetate solution was dried over magnesium sulfate ($MgSO_4$). The magnesium sulfate was then removed by filtration and was rinsed with additional ethyl acetate. The ethyl acetate used to rinse the magnesium sulfate was collected with the DMPA.

The DMPA/ethyl acetate solution was introduced to a round-bottom flask and concentrated to about 20 mL using a conventional rotary evaporator. The round-bottom flask was fitted with an air condenser and a magnetic stir bar. Trimethylorthoformate (1.44 mL, 13.15 mmol) was introduced to the DMPA/ethyl acetate solution in the round-bottom flask. While stirring, the mixture was brought to a mild reflux at a temperature of about the boiling point of ethyl acetate (about 77° C.). Constituents of the mixture having lower boiling points than ethyl acetate (i.e., methanol) were removed by a conventional fractional distillation process. Additional ethyl acetate was added to the round-bottom flask as necessary to maintain a volume substantially equal to an initial reaction volume (about 20 mL). The reaction was monitored by TLC (ethyl acetate) until substantially all of the 5-methoxystyphnic acid was converted to 1,3,5-trimethoxy-2,4,6-trinitrobenzene. The resulting solution was added to a separatory funnel and washed with 10% aqueous sodium bicarbonate. The aqueous layer was removed and discarded and the organic layer was dried over magnesium sulfate. The magnesium sulfate was removed by a conventional filtration process and was rinsed with a minimal amount of ethyl acetate. Additional ethyl acetate was introduced to the filtrate to form a mixture of 1,3,5-trimethoxy-2,4,6-trinitrobenzene and ethyl acetate.

Figure 2:
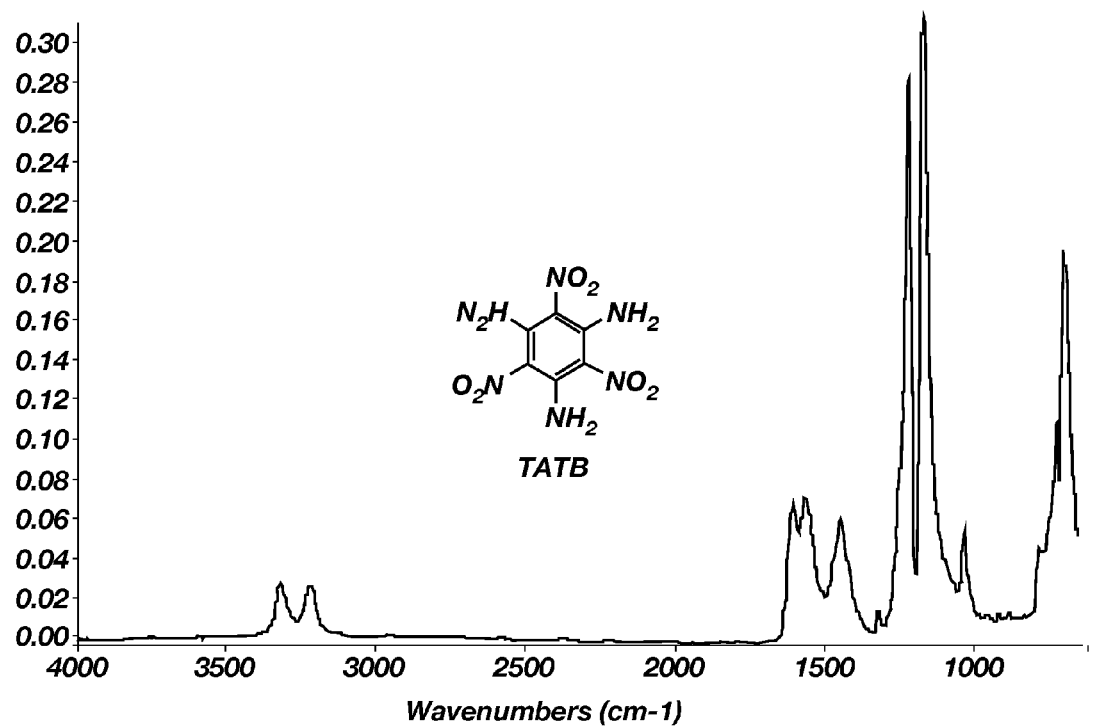
FIG. 2 is a spectrum of TATB formed by the process described in Example 1 obtained using Fourier transform infrared spectroscopy.

The 1,3,5-trimethoxy-2,4,6-trinitrobenzene/ethyl acetate mixture was added to a round-bottom flask equipped with a magnetic stir bar. About 1 atm of anhydrous ammonia gas was introduced into the round-bottom flask. The 1,3,5-trimethoxy-2,4,6-trinitrobenzene/ethyl acetate mixture was stirred under 1 atm of anhydrous ammonia gas for about 6 hours as the yellowish solid precipitated. The yellowish solid was collected by vacuum filtration, rinsed with ethyl acetate, then water, and dried (water removed) by vacuum filtration. The solid was characterized as TATB by FT-IR and HPLC, the results of which are shown in FIGS. 1 and 2, respectively. The product yield was from about 40% to about 80% crude TATB based on 3,5-DMP. The purity of the TATB was greater than about 92%.

Example 2

Synthesis of TATB from 5-Methoxyresorcinol (5-MR)

Sulfuric acid (10 mL (96%)) is placed in a 25-ml round-bottom flask equipped with a cooling bath and a magnetic stirrer and the round-bottom flask is cooled to about 5° C. Ammonium nitrate (about 3 molar equivalents with respect to 5-MR) is added with stirring to the round-bottom flask at a rate such that the temperature does not exceed about 10° C. The temperature of the round-bottom flask is reduced to about 5° C. and 5-MR is added thereto. The 5-MR is added to the round-bottom flask at a rate such that the temperature does not exceed about 15° C. After addition of the 5-MR, the cooling bath is removed, and the reaction mixture is stirred for about 10 minutes. The reaction mixture is added in a single portion to crushed ice (100 g) and is gently stirred until the ice substantially melts and a solid precipitates in an aqueous solution.

The aqueous solution is added to a separatory funnel and the product, 5-methoxystyphnic acid, is extracted with ethyl acetate. The ethyl acetate solution is chromatographed over silica gel. The silica gel is rinsed with additional ethyl acetate to remove the solid remaining in the silica gel. A solution of the 5-methoxystyphnic acid and ethyl acetate is introduced to a round-bottom flask and is concentrated. The round-bottom flask is fitted with an air condenser and a magnetic stir bar. Trimethylorthoformate (about 4 molar equivalents with respect to 5-methoxystyphnic acid) is introduced to solid/ethyl acetate solution in the round-bottom flask. While stirring, the solid/ethyl acetate solution is brought to a mild reflux at a temperature about equal to a boiling point of ethyl acetate (about 77° C.). Constituents having a lower boiling point than ethyl acetate (i.e., methanol) are removed by a conventional fractional distillation process. Additional ethyl acetate is added to the round-bottom flask as necessary to maintain an initial reaction volume. The reaction is monitored by TLC (ethyl acetate) until substantially all of the 5-methoxystyphnic acid is converted to 1,3,5-trimethoxy-2,4,6-trinitrobenzene (i.e., about 24 hours to about 72 hours). The resulting solution is added to a separatory funnel and washed with 10% aqueous sodium bicarbonate forming an aqueous layer and an organic layer. The aqueous layer is removed and discarded and the organic layer is dried over magnesium sulfate. The magnesium sulfate is removed by a conventional filtration process and is rinsed with a minimal amount of ethyl acetate. Additional ethyl acetate is introduced to the filtrate to form a mixture of 1,3,5-trimethoxy-2,4,6-trinitrobenzene and ethyl acetate.

The 1,3,5-trimethoxy-2,4,6-trinitrobenzene/ethyl acetate mixture is added to a round-bottom flask equipped with a magnetic stir bar. About 1 atm of anhydrous ammonia gas is introduced into the round-bottom flask. The 1,3,5-trimethoxy-2,4,6-trinitrobenzene/ethyl acetate mixture is stirred under 1 atm of anhydrous ammonia gas for about 6 hours as solid (TATB) precipitates. The solid is collected by vacuum filtration, rinsed with ethyl acetate, then water, and dried (water removed) by conventional vacuum filtration.

Example 3

Synthesis of TATB from 1,3,5-Trimethoxybenzene (1,3,5-TMB)

Sulfuric acid is placed in a 25-ml round-bottom flask equipped with a cooling bath and a magnetic stirrer and the round-bottom flask is cooled to about 5° C. Potassium nitrate (about 3 molar equivalents with respect to 1,3,5-TMB) is added with stirring to the round-bottom flask at a rate such that the temperature does not exceed about 10° C. The temperature of the round-bottom flask is reduced to about 5° C. and 1,3,5-TMB (0.25 g (1.49 mmol)) is added thereto. The 1,3,5-TMB is added to the round-bottom flask at a rate such that the temperature does not exceed about 15° C. Vigorous stirring is maintained to prevent concentrating the 1,3,5-TMB in the center of the round-bottom flask. After addition of the 1,3,5-TMB is complete, the temperature of the round-bottom flask is increased to about 55° C. Once at 55° C., the solution is added in a single portion to distilled water (100 mL) resulting in precipitation of a solid. The slurry is added to a separatory funnel and then extracted with ethyl acetate to form a solution of 1,3,5-trimethoxy-2,4,6-trinitrobenzene and ethyl acetate. The 1,3,5-trimethoxy-2,4,6-trinitrobenzene is added to a round-bottom flask equipped with a magnetic stir bar. About 1 atm of anhydrous ammonia gas is introduced into the round-bottom flask. The 1,3,5-trimethoxy-2,4,6-trinitrobenzene/ethyl acetate mixture is stirred under 1 atm of anhydrous ammonia gas for about 6 hours as a yellowish solid (TATB) precipitates. The solid is collected by vacuum filtration, rinsed with ethyl acetate, then water, and dried (water removed) by vacuum filtration.

While the invention is susceptible to implementation with various modifications and in various forms, specific embodiments have been described in detail herein. However, it should be understood that the invention is not intended to be limited to the particular forms disclosed. Rather, the invention is to cover all modifications, equivalents, and alternatives falling within the scope of the invention as defined by the following appended claims.

What is claimed is:

1. A method of producing 1,3,5-triamino-2,4,6-trinitrobenzene, comprising:
   exposing at least one alkoxy derivative of phloroglucinol to a reaction mixture comprising at least one nitrate salt and a sulfuric acid solution to form a nitrated product comprising at least one of a mono-alkoxylated nitrated product and a di-alkoxylated nitrated product;
   reacting the at least one of the mono-alkoxylated nitrated product and the di-alkoxylated nitrated product with an alkoxylating agent to form a 1,3,5-trialkoxy-2,4,6-trinitrobenzene; and
   reacting the 1,3,5-trialkoxy-2,4,6-trinitrobenzene with an aminating agent to form 1,3,5-triamino-2,4,6-trinitrobenzene.

2. The method of claim 1, wherein exposing at least one alkoxy derivative of phloroglucinol to a reaction mixture comprises exposing the at least one alkoxy derivative of phloroglucinol to a reaction mixture comprising the at least one nitrate salt and a sulfuric acid solution comprising from approximately 90% by weight to approximately 100% by weight of sulfuric acid.

3. The method of claim 1, wherein exposing at least one alkoxy derivative of phloroglucinol to a reaction mixture comprising at least one nitrate salt and a sulfuric acid solution comprises exposing the at least one alkoxy derivative of phloroglucinol to a reaction mixture comprising at least one nitrate salt selected from the group consisting of sodium nitrate, potassium nitrate, ammonium nitrate, calcium nitrate, and magnesium nitrate and the sulfuric acid solution.

4. The method of claim 1, further comprising forming the reaction mixture by adding the at least one nitrate salt into the sulfuric acid solution at a temperature in a range of from about 0° C. to about 10° C.

5. The method of claim 1, wherein exposing at least one alkoxy derivative of phloroglucinol to a reaction mixture comprises exposing at least one of 5-methoxyresorcinol and 3,5-dimethoxyphenol to the reaction mixture to form the nitrated product.

6. The method of claim 1, wherein reacting at least one of a mono-alkoxylated nitrated product and a di-alkoxylated nitrated product with an alkoxylating agent and reacting the 1,3,5-trialkoxy-2,4,6-trinitrobenzene with an aminating agent are each performed in a single organic solvent.

7. The method of claim 1, wherein reacting the at least one of the mono-alkoxylated nitrated product and the di-alkoxylated nitrated product with an alkoxylating agent and reacting the 1,3,5-trialkoxy-2,4,6-trinitrobenzene with an aminating agent are each performed in ethyl acetate.

8. The method of claim 7, further comprising extracting the nitrated product from the reaction mixture with ethyl acetate.

9. The method of claim 1, wherein reacting the 1,3,5-trialkoxy-2,4,6-trinitrobenzene with an aminating agent to form 1,3,5-triamino-2,4,6-trinitrobenzene comprises reacting the 1,3,5-trialkoxy-2,4,6-trinitrobenzene with ammonia.

10. The method of claim 1, wherein reacting the at least one of the mono-alkoxylated nitrated product and the di-alkoxylated nitrated product with an alkoxylating agent to form a 1,3,5-trialkoxy-2,4,6-trinitrobenzene comprises reacting the at least one of the mono-alkoxylated nitrated product and the di-alkoxylated nitrated product with a trialkyl orthoformate in ethyl acetate to form a solution comprising the 1,3,5-trialkoxy-2,4,6-tri-nitrobenzene.

11. A method of producing 1,3,5-triamino-2,4,6-trinitrobenzene, comprising:
   exposing 1,3,5-trimethoxybenzene to a reaction mixture comprising at least one nitrate salt and a sulfuric acid solution to form 1,3,5-trimethoxy-2,4,6-trinitrobenzene; and
   reacting the 1,3,5-trialkoxy-2,4,6-trinitrobenzene with an aminating agent.

12. The method of claim 11, further comprising forming the reaction mixture by combining the at least one nitrate salt and a sulfuric acid solution comprising from approximately 90% by weight to approximately 100% by weight of sulfuric acid.

13. The method of claim 11, further comprising extracting 1,3,5-trimethoxy-2,4,6-trinitrobenzene with ethyl acetate to form a slurry.

14. The method of claim 11, wherein exposing 1,3,5-trimethoxybenzene to a reaction mixture comprising at least one nitrate salt and a sulfuric acid solution comprises exposing the 1,3,5-trimethoxybenzene and the reaction mixture to a temperature within a range of from about 0° C. to about 55° C.

15. The method of claim 11, wherein exposing 1,3,5-trimethoxybenzene to a reaction mixture comprising at least one nitrate salt and a sulfuric acid solution comprises exposing 1,3,5-trimethoxybenzene to a reaction mixture comprising at least one nitrate salt selected from the group consisting of sodium nitrate, potassium nitrate, ammonium nitrate, calcium nitrate, and magnesium nitrate and the sulfuric acid solution.

16. A method of producing 1,3,5-trimethoxy-2,4,6-trinitrobenzene, comprising:
   exposing at least one alkoxy derivative of phloroglucinol to a reaction mixture comprising at least one nitrate salt and a sulfuric acid solution to form a nitrated product; and
   reacting at least one of the mono-alkoxylated nitrated product and the di-alkoxylated nitrated product with an alkoxylating agent in an organic solvent to form 1,3,5-trimethoxy-2,4,6-trinitrobenzene.

17. The method of claim 16, wherein exposing at least one alkoxy derivative of phloroglucinol to a reaction mixture comprising at least one nitrate salt and a sulfuric acid solution to form a nitrated product comprises exposing at least one of 5-methoxyresorcinol and 3,5-dimethoxyphenol to the reaction mixture comprising the at least one nitrate salt and the sulfuric acid solution to form the nitrated product.

18. The method of claim 16, wherein reacting the at least one of the mono-alkoxylated nitrated product and the di-alkoxylated nitrated product with an alkoxylating agent in an organic solvent comprises reacting the at least one of the mono-alkoxylated nitrated product and the di-alkoxylated nitrated product with the alkoxylating agent in ethyl acetate.

19. The method of claim 16, wherein reacting the at least one of a mono-alkoxylated nitrated product and a di-alkoxylated nitrated product with an alkoxylating agent in an organic solvent comprises reacting the at least one of the mono-alkoxylated nitrated product and the di-alkoxylated nitrated product with a trialkyl orthoformate in the organic solvent.

* * * * *

UNITED STATES PATENT AND TRADEMARK OFFICE
CERTIFICATE OF CORRECTION

PATENT NO. : 7,910,776 B2  
APPLICATION NO. : 12/484985  
DATED : March 22, 2011  
INVENTOR(S) : Straessler et al.

Page 1 of 1

It is certified that error appears in the above-identified patent and that said Letters Patent is hereby corrected as shown below:

On the title page:
In ITEM [56] References Cited
    OTHER PUBLICATIONS
    Column 2, line 43      change "New York, NY, p. 29. Ott, D.G., et al.,"
                                    to --New York, NY, p. 29.
                                    Ott, D.G., et al.,--

In the specification:
    COLUMN 1, LINE 21,      change "Ser." to --Ser. No.--
    COLUMN 4, LINE 67,      change "in co-pending" to --in--

Signed and Sealed this
Twenty-fifth Day of February, 2014

Michelle K. Lee
*Deputy Director of the United States Patent and Trademark Office*